United States Patent [19]

Harrison et al.

[11] Patent Number: 4,960,960
[45] Date of Patent: Oct. 2, 1990

[54] HYDROGENATION PROCESS

[75] Inventors: George E. Harrison, Billericay; John R. Hensman, Letchworth, both of England

[73] Assignee: Davy McKee (London) Limited, London, England

[21] Appl. No.: 254,933

[22] PCT Filed: Feb. 5, 1988

[86] PCT No.: PCT/GB87/00070
§ 371 Date: Oct. 5, 1988
§ 102(e) Date: Oct. 5, 1988

[87] PCT Pub. No.: WO88/05767
PCT Pub. Date: Aug. 11, 1988

[30] Foreign Application Priority Data

Feb. 6, 1987 [GB] United Kingdom ............... 8702654

[51] Int. Cl.$^5$ ............... C07C 29/132; C07C 29/14; C07C 29/17; C07C 29/20
[52] U.S. Cl. .................. 568/881; 260/409; 260/413; 568/835; 568/861; 568/863; 585/265
[58] Field of Search ............. 568/881, 835, 861, 863; 585/357, 265; 260/413 R, 409

[56] References Cited

U.S. PATENT DOCUMENTS 3,301,909 1/1967 Kawasaki et al. ............... 568/881
4,626,604 12/1986 Hiles et al. ............... 568/881

FOREIGN PATENT DOCUMENTS 0073129 3/1983 European Pat. Off. .
2142010 1/1985 United Kingdom .

Primary Examiner—J. E. Evans
Attorney, Agent, or Firm—Bernard, Rothwell & Brown

[57] ABSTRACT

Hydrogen is supplied first to a last hydrogenation zone, and gases recovered from the last hydrogenation zone are passed to the first hydrogenation zone of a continuous multi-zone liquid phase process for hydrogenating an organic compound to a corresponding hydrogenation product. The organic compound, with a suitable diluent or recycle hydrogenation product, flows successively through the zones beginning with the first and ending with the last hydrogenation zone to undergo hydrogenation with the hydrogenation product being recovered from the last hydrogenation zone.

12 Claims, 1 Drawing Sheet

HYDROGENATION PROCESS

This invention relates to a catalytic hydrogenation process.

Heterogeneous catalytic hydrogenation processes of various kinds are widely practised on a commercial scale and are used for hydrogenation of a wide variety of unsaturated organic compounds. Typically such hydrogenation reactions are conducted at a pressure of from about 1 bar to about 300 bar and at a temperature in the range of from about 40° C. to about 350° C. Examples include hydrogenation of aldehydes to alcohols, of unsaturated hydrocarbons to saturated hydrocarbons, of acetylene-derived chemicals to saturated materials, of unsaturated fatty acids to saturated fatty acids, of ketones to secondary alcohols, of esters of unsaturated fatty acids to esters of partially or fully hydrogenated fatty acids, and of certain sugars to polyhydroxyalcohols. Thus cyclohexanol is produced commercially by catalytic hydrogenation of cyclohexanone, and iso-propanol by catalytic hydrogenation of acetone. An example of hydrogenation of an unsaturated hydrocarbon is the production of cyclohexane from benzene. Typical catalysts for such hydrogenation reactions include Group VIII metal catalysts, such as nickel, palladium and platinum. Production of butane-1,4-diol by hydrogenation of but-2-yn-1,4-diol is an example of hydrogenation of an acetylene-derived chemical. A suitable catalyst for this reaction has been described as a granular nickel-copper-manganese on silica gel. The production of stearic acid by catalytic hydrogenation of the corresponding unsaturated acids, linoleic acid and linolenic acid, at a temperature of about 150° C. and at a pressure of about 14.75 bar to about 32 bar and using a nickel, cobalt, platinum, palladium, chromium or zinc catalyst, is an example of the hydrogenation of unsaturated fatty acids to yield saturated fatty acids. So-called "hardening" of vegetable oils is an example of hydrogenation of esters of unsaturated fatty acids. As examples of hydrogenation of sugars to polyhydroxyalcohols there can be mentioned hydrogenation of aldoses to hexahydroxyalcohols, for example hydrogenation of D-glucose to sorbitol and of D-mannose to mannitol.

An important route to $C_3$ and higher alkanols involves hydroformylation of alpha-olefins, such as ethylene, propylene, and butene-1, to yield the corresponding aldehyde having one more carbon atom than the starting olefin. Thus ethylene yields propionaldehyde and propylene yields a mixture of n- and isobutyraldehydes (with the n-isomer usually predominating). These aldehydes yield the corresponding alkanols, e.g. n-propanol and n-butanol, upon catalytic hydrogenation. The important plasticiser alcohol, 2-ethylhexanol, is made by alkali-catalysed condensation of n-butyraldehyde to yield the unsaturated aldehyde, 2-ethyl-hex-2-enal, which is then hydrogenated to yield the desired 2-ethylhexanol. Although the preferred catalysts for such aldehyde hydrogenation reactions used to be Group VIII metal catalysts, such as nickel, palladium or platinum, the use of a solid catalyst comprising a reduced mixture of CuO and ZnO under vapour phase conditions has also been proposed (see EP-A-No. 0008767 and U.S. Pat. No. 2,549,416). Molybdenum sulphide supported on an activated carbon carrier has also been suggested in GB-A-No. 765,972. The hydrogenation of an aldehyde feed containing ring-type sulphur compounds using a reduced mixture of oxides or hydroxides of copper and zinc is described in U.S. Pat. No. 4,052,467. Copper chromite has also been used as an aldehyde hydrogenation catalyst.

Catalytic hydrogenation is in all the above cases a heterogeneous process. It may be operated as a liquid phase process or as a vapour phase process. A review of some of the factors involved in designing heterogeneous gas and vapour phase reaction systems appeared in "Chemical Engineering", July 1955, in an article entitled "Moving Bed—Processes ... New Applications", at pages 198 to 206 (see in particular pages 204 and 205 thereof).

There have been various prior proposals to operate hydrogenation proceses in several catalytic stages connected in series. For example, a vapour phase aldehyde hydrogenation process is described in U.S. Pat. No. 4,451,677 which involves use of a plurality of adiabatically operated catalytic hydrogenation stages connected in series.

In conventional multi-stage hydrogenation processes the hydrogen-containing gas and the material to be hydrogenated are fed through the plant in co-current or in counter-current fashion. In order to achieve good economy of hydrogen usage it is usual to recycle gas within the plant. Hence in designing the plant account must be taken of the circulating inert gases (e.g. $N_2$, Ar, $CH_4$ and the like) which are inevitably present in the circulating gas of a commercial plant.

The present invention seeks to provide an improved liquid phase hydrogenation process in which essentially 100% hydrogenation of the aldehyde or other unsaturated organic compound to the desired hydrogenation product can be achieved, without significant formation of byproducts.

It further seeks to provide a multi-stage hydrogenation process in which the use of gas recycle compressors can be obviated. Additionally it seeks to provide a process for hydrogenation of a wide variety of unsaturated organic compounds which can be operated with excellent economy of hydrogen usage without the need for recycle of hydrogen-containing gases.

According to the present invention a continuous process for hydrogenating an unsaturated organic compound to a corresponding hydrogenation product comprises:

(a) providing a hydrogenation plant comprising first and second hydrogenation zones connected in series each containing a charge of a solid heterogeneous hydrogenation catalyst;

(b) continuously supplying to an upper part of the first hydrogenation zone (i) a hydrogen-containing gas and (ii) a liquid phase containing the unsaturated organic compound dissolved in a compatible diluent therefor;

(c) maintaining the first hydrogenation zone under temperature and pressure conditions conducive to hydrogenation;

(d) allowing liquid phase to pass downwardly through the first hydrogenation zone;

(e) continuously recovering an intermediate reaction product from a lower part of the first hydrogenation zone;

(f) recovering a gaseous effluent stream from a lower part of the first hydrogenation zone;

(g) supplying intermediate reaction product from step (e) in liquid form to an upper part of the second hydrogenation zone;

(h) maintaining the second hydrogenation zone under temperature and pressure conditions conducive to hydrogenation;

(i) allowing intermediate liquid reaction product to pass downwardly through the second hydrogenation zone;

(j) supplying a hydrogen-containing feed gas to an upper part of the second hydrogenation zone;

(k) recovering a gaseous effluent stream from a lower part of the second hydrogenation zone;

(l) Supplying material of the gaseous effluent stream of step (k) to form the hydrogen-containing gas of step (b);

(m) recovering a liquid hydrogenation product containing stream from a lower part of the second hydrogenation zone; and (n) purging material of the gaseous effluent stream of step (f) from the hydrogenation plant.

DESCRIPTION OF THE PREFERRED EMBODIMENTS

Figure 1:
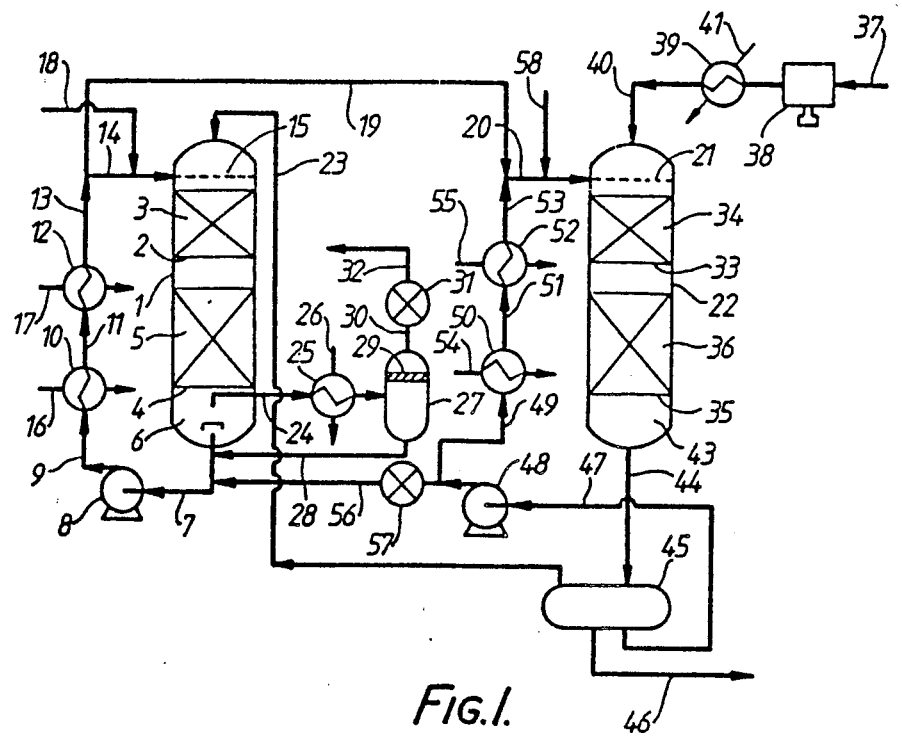
FIG. 1 is a simplified flow diagram of an aldehyde hydrogenation plant in accordance with the invention.

The process of the invention is not specific to any particular hydrogenation reaction or to any particular catalyst composition. However, in general the hydrogenation conditions used in the first and second hydrogenation zones include use of a pressure of from about 1 bar to about 300 bar and of a temperature of from about 40° C. to about 300° C.

The process of the invention can be applied, for example to the hydrogenation of unsaturated hydrocarbons to saturated hydrocarbons. Typical of such a reaction is the production of cyclohexane from benzene. This hydrogenation can be carried out according to the invention using a nickel, palladium or platinum catalyst in each catalytic stage and a temperature of from about 100° C. to about 350° C. and a pressure of from about 5 bar to about 30 bar. This reaction is exothermic. The use of high temperatures is normally recommended so as to maximise conversion of benzene to cyclohexane, but isomerisation of cyclohexane to methyl cyclopentane, which is extremely difficult to separate from cyclohexane, can occur in the aforementioned conventional procedures.

Production of secondary alcohols by reduction of ketones is another appropriate hydrogenation reaction to which the invention can be applied. Examples of such reactions include production of iso-propanol from acetone and of cyclohexanol from cyclohexanone.

Another example of a hydrogenation reaction to which the present invention can be applied is the production of butane-1,4-diol by hydrogenation of but-2-yn-1,4-diol. This can be carried out using a catalyst which is a granular nickel-copper-manganese on silica gel at a pressure of from about 200 bar to about 300 bar in each catalytic stage. A typical inlet temperature to the first hydrogenation zone is about 40° C., when the catalyst is freshly reduced.

A further example of a hydrogenation reaction to which the process of the invention can be applied is the production of stearic acid by hydrogenation of linoleic acid, of linolenic acid, or of a mixture thereof. This can be carried out using a nickel, cobalt, platinum, palladium, chromium or zinc catalyst at a pressure of from about 14.75 bar to about 32 bar and an inlet temperature to the first hydrogenation zone of about 150° C.

Other examples of hydrogenation processes to which the invention can be applied include "hardening" of vegetable oils and hydrogenation of sugars, (for example, hydrogenation of aldoses, such as D-glucose or D-mannose, to the corresponding hexahydroxyalcohols, such as sorbitol and mannitol).

A particularly preferred type of hydrogenation reaction is the production of alcohols from aldehydes. Such aldehydes generally contain from 2 to about 20 carbon atoms and may in the case of those aldehydes containing 3 or more carbon atoms include one or more unsaturated carbon-carbon bonds besides the unsaturated —CHO group. Thus as used herein the term "aldehyde" includes both saturated and unsaturated aldehydes, that is to say aldehydes wherein the only hydrogenatable group is the aldehyde group, —CHO, itself (such as alkanals) and aldehydes which contain further hydrogenatable groups such as olefinic groups, >C=C<, in addition to the aldehyde group, —CHO (such as alkenals). Typical aldehydes include n- and iso-butyraldehydes, n-pentanal, 2-methylbutanal, 2-ethylhex-2-enal, 2-ethylhexanal, 4-t-butoxybutyraldehyde, $C_{10}$-"OXO"-aldehydes (e.g. 2-propylhept-2-enal), undecanal, crotonaldehyde and furfural, as well as mixtures of two or more thereof. Such aldehydes and mixtures of aldehydes can be produced by hydroformylation of an olefin in the presence of a cobalt catalyst or a rhodium complex catalyst, according to the equation:

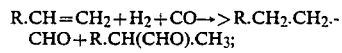

$$R.CH=CH_2 + H_2 + CO \rightarrow R.CH_2.CH_2.CHO + R.CH(CHO).CH_3;$$

where R is a hydrogen atom or an alkyl radical. The ratio of the n-aldehyde to the iso-aldehyde in the product depends to a certain extent on the selected hydroformylation conditions and upon the nature of the hydroformylation catalyst used. Although cobalt catalysts were formerly used, more recently the use of rhodium complex catalysts has been preferred since these offer the advantages of lower operating pressure, ease of product recovery, and high n-/iso-aldehyde molar ratios. Typical operating conditions for such rhodium complex hydroformylation catalysts can be found in U.S. Pat. Nos. 3,527,809, 4,148,830, EP-A-Nos. 0096986, 0096987, and 0096988. In such hydroformylation processes the aldehyde or aldehyde products can be recovered in admixture with unreacted olefin and its hydrogenation product, i.e. the corresponding paraffin. Such crude reaction products can be used as starting material in the process of the invention. Further aldehydes can be obtained by condensation reactions; for example, 2-ethylhex-2-enal can be made by condensation of 2 moles of n-butyraldehyde and 2-propylhept-2-enal by condensation of 2 moles of n-valeraldehyde. Examples of aldehyde hydrogenation reactions are the production of n-butanol from n-butyraldehyde, of 2-ethylhexanol from 2-ethylhex-2-enal, of 2-propylheptanol from 2-propylhept-2-enal, of undecanol from undecanal, and of 4-t-butoxybutanol from 4-t-butoxybutyraldehyde. The invention is used to special advantage for hydrogenation of aldehydes containing from about 7 to about 17 carbon atoms to the corresponding alkanols. In such aldehyde hydrogenation reactions there can be used any of the conventionally used metal catalysts, such as Ni, Pd or Pt, or copper chromite, or a reduced mixture of CuO and ZnO of the type disclosed in EP-A-No. 0008767 and U.S. Pat. No. 2,549,416. According to EP-A-0008767 catalysts of this type under appropriately selected reaction conditions give rise to negligible formation of byproducts, such as ethers and hydrocarbons and also to small amounts only of "heavies" formation (such as esters) when aldehydes are hydrogenated.

Other aldehyde hydrogenation catalysts include cobalt compounds; nickel compounds which may contain small amounts of chromium or another promoter; mixtures of copper and nickel and/or chromium; and other Group VIII metal catalysts, such at Pt, Pd, Rh and mixtures thereof, on supports, such as carbon, silica, alumina and silica-alumina. The nickel compounds are generally deposited on support materials such as alumina or kieselguhr.

The first and second hydrogenation zones may each include two or more beds of catalyst. Conveniently, however, each hydrogenation zone comprises a single catalyst bed. The individual beds of catalyst may be provided in separate vessels; in a preferred embodiment, however, the first and second hydrogenation zones comprise lower and upper beds respectively of catalyst housed within a single reaction vessel.

Thus in a preferred process the first and second hydrogenation zones comprise respective beds of catalyst mounted one above another within a reaction vessel, with the bed or beds of the second hydrogenation above the bed or beds of the first hydrogenation zone. In this arrangement, in step (n), purging of material of the gaseous effluent of step (f) is effected via a purge gas system connected to the reaction vessel at a point or points below the bed or beds of catalyst of the first hydrogenation zone. An alternative preferred process is one in which the first and second hydrogenation zones are provided in separate reaction vessels connected in series, in which the reaction vessel of the first hydrogenation zone is connected to the reaction vessel of the second hydrogenation zone by way of a conduit for liquid intermediate reaction product, and in which the lower end of the reaction vessel of the first hydrogenation zone is provided with a gas purge line for purging gaseous effluent therefrom.

The hydrogen-containing feed gas supplied to the second hydrogenation zone preferably contains a major amount of hydrogen and at most a minor amount of one or more inert gases, such as nitrogen, methane, other low molecular weight hydrocarbons, such as ethane, propane, n-butane and iso-butane, carbon oxides, neon, argon or the like. Preferred hydrogen-containing feed gases are accordingly gases containing at least about 50 mole % up to about 95 mole % or more (e.g. about 99 mole %) of $H_2$ with the balance comprising one or more of $N_2$, CO, $CO_2$, Ar, Ne, $CH_4$ and other low molecular weight saturated hydrocarbons. In some cases, e.g. when using nickel catalysts, the presence of CO and $CO_2$ cannot be tolerated and the total carbon oxides concentration in the hydrogen-containing feed gas should not be more than about 5 ppm. Such hydrogen-containing feed gases can be obtained in conventional manner from synthesis gas and other usual sources of hydrogen-containing gases, followed by appropriate pre-treatment to remove impurities, such as sulphurous impurities (e.g. $H_2S$, COS, $CH_3SH$, $CH_3SCH_3$, and $CH_3SSCH_3$) and halogen-containing impurities (e.g. HCl and $CH_3Cl$) which would exert a deleterious influence on catalytic activity, i.e. catalyst inhibition, poisoning or deactivation. Preparation of suitable hydrogen-containing feed gases will accordingly be effected according to usual production techniques and forms no part of the present invention. Thus the hydrogen-containing feed gas may be, for example, a 94 mole % hydrogen stream produced by steam reforming of natural gas followed by the water gas shift reaction:

$$CO + H_2O = H_2 + CO_2,$$

then by carbon dioxide removal to give a gas containing about 1 to about 2 mole % $CO + CO_2$ and finally by methanation to give a gas containing only a few ppm of carbon oxides. Alternatively it may be a substantially pure $H_2$ stream formed by subjecting the same 94 mole % $H_2$ stream to purification, e.g. by pressure swing absorption.

The liquid phase supplied to the upper part of the first hydrogenation zone contains the unsaturated organic compound dissolved in a compatible diluent therefor. The purpose of the diluent is to act as a heat sink and to limit the temperature rise within the first hydrogenation zone to an acceptable limit. The concentration of unsaturated organic compound in the liquid phase is accordingly preferably selected in dependence on the expected acceptable temperature rise across the first hydrogenation zone; such temperature rise should not be so great as to cause more than a minor amount of vaporisation of the liquid phase in the upper part of the first hydrogenation zone or to cause thermal damage to the catalyst, to the reactants or to the hydrogenation product. When the desired hydrogenation product and/or the diluent is relatively volatile, then it is possible to conduct the process so that a significant amount of vaporisation, or even complete vaporisation, occurs in the lower part of the first hydrogenation zone due to the adiabatic temperature rise caused by the heat released by the hydrogenation reaction. Such vaporisation is not deleterious to operation of the process, so long as the reaction mixture remains in the liquid phase in the upper part of the first hydrogenation zone. In this case the intermediate reaction product in the vapour phase exiting the first hydrogenolysis zone is desirably condensed for supply to the second hydrogenation zone in liquid form.

Generally speaking the liquid phase supplied to the first hydrogenation zone contains at least about 1 mole % of the unsaturated organic compound up to about 50 mole %, more preferably in the range of from about 5 mole % up to about 30 mole %, the balance being diluent or diluents.

The diluent can be any convenient inert liquid or mixture of liquids that is compatible with the unsaturated organic compound, with any intermediate product or by-product, and with the desired hydrogenation product. In many cases the hydrogenation product itself can be used as the compatible diluent or as a part of the compatible diluent. Hence, when hydrogenating an aldehyde, for example, the diluent can be the product alcohol obtained upon hydrogenation of the aldehyde. In this case the process of the invention includes the further step of recycling a part of the liquid hydrogenation product stream of step (m) for admixture with the unsaturated organic compound to form the liquid phase (ii) of step (b). Alternatively aldehyde condensation products, such as the dimers, trimers and higher condensation products of the type disclosed in GB-A-No. 1338237, can be used as diluent. If the unsaturated organic compound used as starting material is a solid or if the hydrogenation product or an intermediate product is a solid, then an inert solvent will usually be used. Similarly, use of a solvent may be desirable in cases in which byproduct formation is a problem. For example, hydrazobenzene is a potential byproduct of the hydrogenation of nitrobenzene to yield aniline; in such a case it is desirable to dissolve the unsaturated organic compound, such as nitrobenzene, in a solvent, such as ethanol, in order to limit formation of an undesirable byproduct, such as hydrazobenzene. In this case it is also highly advantageous to include a minor amount of ammonia in the ethanol solvent as ammonia further limits the formation of byproducts such as azobenzene, azoxybenzene or hydroazobenzene.

The first hydrogenation zone may comprise an adiabatic reactor, a reactor with an internal cooling coil, or a shell and tube reactor. In the case of a shell and tube reactor the catalyst may be packed in the tubes with coolant passing through the shell or it may be the shell that is packed with catalyst with coolant flow through the tubes. The first hydrogenation zone is generally operated as a trickle bed reactor. In this case the hydrogen containing gas of step (b) is generally admixed with the liquid phase upstream from the first hydrogenation zone and is partly dissolved therein. At the upper end of the first hydrogenation zone the concentration of unsaturated organic compound is at its highest in the liquid phase; hence the rate of hydrogenation is greatest at the upper end of the first hydrogenation zone. As the liquid phase passes downwardly through the first hydrogenation zone co-currently with the hydrogen it becomes depleted in respect of hydrogenatable material and to some extent in respect of dissolved hydrogen and the partial pressure of any inert gas or gases present rises and the partial pressure of hydrogen falls as the hydrogen is consumed by the chemical reactions taking place in the first hydrogenation zone. Hence at the lower end of the first hydrogenation zone the driving force for the hydrogenation reaction is relatively low. The intermediate reaction product exiting the lower end of the first hydrogenation zone accordingly usually still contains a minor amount of chemically unsaturated hydrogenatable material. Typically the intermediate reaction product contains from about 0.01 mole % to 0.5 mole %, up to about 5 mole % or more of chemically unsaturated hydrogenatable organic material.

As already mentioned, the unsaturated organic compound used as starting material may include two or more hydrogenatable unsaturated groups which may undergo more or less selective hydrogenation in passage through the first hydrogenation zone. For example, when an olefinically unsaturated aldehyde (such as 2-ethylhex-2-enal) is hydrogenated, the olefinic bond tends to be hydrogenated first, before the aldehyde group, so that the saturated aldehyde (such as 2-ethylhexanal) is a recognisable intermediate product. However, some hydrogenation of the aldehyde group may occur prior to hydrogenation of the olefinic linkage, so that 2-ethylhex-2-enol is an alternative intermediate product but is generally formed in lesser amounts. Each of these intermediates can then undergo hydrogenation to the desired alcohol product, e.g. 2-ethylhexanol.

When the unsaturated organic compound used as starting material contains only a single hydrogenatable linkage, then the unsaturated hydrogenatable organic material in the intermediate reaction product exiting the first hydrogenation zone will comprise the unsaturated organic compound itself. However, when the unsaturated organic compound used as starting material contains more than one hydrogenatable unsaturated linkage, then the unsaturated hydrogenatable organic material in the intermediate reaction product exiting the first hydrogenation zone will be selected from the starting material and any partially hydrogenated intermediates. For example, when hydrogenating 2-ethylhex-2-enal, the unsaturated organic material in the intermediate reaction product may be selected from 2-ethylhex-2-enal, 2-ethylhexanal, 2-ethylhex-2-enol, and a mixture of two or more thereof.

Generally speaking the hydrogenation conditions in the first hydrogenation zone are selected so as to effect hydrogenation of from about 75% to about 99% or more of the hydrogenatable unsaturated groups present in the unsaturated organic material supplied to the first hydrogenation zone. Typically the hydrogenation is completed to an extent of from about 85% to about 99.5% in the first hydrogenation zone. In some cases, however, the extent of hydrogenation may be higher than this, e.g. about 99.8% or even up to about 99.99%, in the first hydrogenation zone. Such hydrogenation conditions include supply of hydrogen-containing gas of step (b) to the upper part of the first hydrogenation zone in an amount sufficient to supply an amount of hydrogen that is greater than or equal to the stoichiometric quantity required to effect the desired degree of hydrogenation in the first hydrogenation zone. Usually it will be desirable to limit the supply of hydrogen-containing gas thereto so as to provide as nearly as possible such stoichiometric quantity of hydrogen and thereby to minimise hydrogen losses in the purge stream from the plant. Although the rate of supply of hydrogen-containing gas to the first hydrogenation zone will be to some extent dependent upon its composition, it will generally be preferred to limit the rate of supply so as to provide not more than about 110%, and even more preferably not more than about 105% (e.g. about 102%), of the stoichiometric quantity required to effect the desired degree of hydrogenation in the first hydrogenation zone.

The hydrogenation conditions will also be selected so that at least an upper part of the first hydrogenation zone is operated as a trickle bed reactor. Hence the rate of supply of the liquid feed will be limited by considerations such as the catalyst particle size and shape, the cross section of the reactor, and similar design factors, such as the pressure drop across the or each catalyst bed, which must not be so high as to crush the catalyst.

The composition of the liquid feed will depend upon factors such as the exothermicity of the hydrogenation reaction, the maximum permissible temprature rise in the first hydrogenation zone, the design of the first hydrogenation zone, and the maximum permissible rate of supply to the first hydrogenation zone. When operating under adiabatic conditions the unsaturated organic compound (e.g. aldehyde):inert diluent molar ratio typically ranges from about 1:3 to about 1:10 and the rate of supply of liquid phase to the first hydrogenation zone ranges up to a rate corresponding to supply of unsaturated organic compound of about 8 moles per liter of catalyst per hour or more, e.g. up to about 10 or even 12 moles of aldehyde or other unsaturated organic compound per liter of catalyst per hour. If, however, provision is made for cooling the first hydrogenation zone as, for example, by use of internal cooling coils within the catalyst bed or by use of a shell and tube reactor, then a higher concentration of unsaturated organic compound can be used; hence in this case the unsaturated organic compound:inert diluent molar ratio typically ranges from about 1:1 up to about 1:10.

The inlet temperature to each of the hydrogenation zones will in each case be at least as high as the threshold temperature for the reaction and will be selected in dependence on the nature of the hydrogenation reaction. It will normally lie in the range of from about 40° C. to about 300° C., whilst the operating pressure typically lies in the range of from about 1 bar to about 300 bar. For example when hydrogenating an aldehyde by the process of the invention the inlet temperature to the first hydrogenation zone is typically from about 90° C. to about 220° C. and the pressure is typically from about 5 to about 50 bar.

Besides the unsaturated hydrogenatable organic material and the hydrogenation product and diluent (if different from the hydrogenation product), the intermediate liquid reaction product leaving the first hydrogenation zone also contains dissolved inert gases and hydrogen. The gas phase leaving the first hydrogenation zone contains a higher level of inert gases than the hydrogen-containing gas supplied to the upper part of the first hydrogenation zone because hydrogen has been removed by the hydrogenation reaction in passage through the first hydrogenation zone.

In the second hydrogenation zone the intermediate reaction product from the first hydrogenation zone is fed in liquid form in co-current with a downward flow of the hydrogen-containing feed gas. The second hydrogenation zone can be operated on a once-through basis; alternatively the intermediate reaction can be admixed with recycled product, recovered from the lower end of the second hydrogenation zone so that the second hydrogenation zone is operated on a partial recycle basis. This may be desirable from the standpoint of fluid bed dynamics so as to ensure that the or each bed of catalyst is adequately wetted.

An effluent stream comprising inert gases and hydrogen is taken from the lower end of the first hydrogenation zone. This may be passed through a condenser in order to substantially recover any vaporised organic compounds therein. The resulting condensate is conveniently returned to the top of the first hydrogenation zone.

The catalyst beds of the first and second hydrogenation zones will usually be supported on a suitable grid. When both beds are mounted in the same vessel, liquid intermediate reaction product from the first hydrogenation zone may simply be allowed to drop straight on top of the catalyst bed of the second hydrogenation zone. Usually, however, it will be desirable to collect and then to redistribute the liquid intermediate reaction product evenly over the upper surface of the catalyst bed of the second hydrogenation zone with the aid of a suitable liquid distribution device. In some cases it may be desirable to collect and redistribute liquid within the first and/or second hydrogenation zones.

In a preferred process according to the invention for hydrogenation of an aldehyde the entry temperature to the first hydrogenation zone lies in the range of from about 90° C. to about 220° C. and the pressure lies in the range of from about 5 bar to about 50 bar.

In operation of the process of the invention, under steady state conditions, the composition of the gas (whether dissolved in the liquid phase or present in the gaseous state) exhibits a significant variation between different parts of the plant. Thus, for example, the partial pressure of hydrogen is highest in each of the hydrogenation zones at the respective gas inlet end thereof and lowest at the exit end for gaseous effluent therefrom, whilst the combined partial pressures of any inert materials present is lowest at the respective gas inlet ends to the hydrogenation zones and highest at the exit ends for gaseous effluent therefrom. Under suitable operating conditions it is possible to operate the process of the invention so that the effluent gases contain a very small concentration of hydrogen (e.g. 5 mole % or less) and consist predominantly of inert gases (e.g. $N_2$, Ar, $CH_4$ etc.). In this case the effluent gas stream from the plant is relatively small and consequently hydrogen losses are minimal.

Because the inert gases are automatically concentrated in the gaseous effluent stream, it is not necessary on economic grounds to recycle the gaseous effluents from the hydrogenation zones so as to obtain efficient usage of hydrogen. Recycle of gas is necessary in conventional multi-stage co-current or counter-current hydrogenation processes in order to achieve efficiency of operation. Moreover, as it is not necessary to recycle a gas stream which contains appreciable concentrations of inert gases so as to achieve satisfactory economy of hydrogen consumption, the total operating pressure of the plant can be reduced; hence the construction costs can be reduced as the plant not only operates at a lower pressure but also no gas recycle compressor is needed. The absence of a gas recycle compressor, which is in itself an expensive item of equipment, means also that the civil engineering work associated with its installation, such as provision of a mounting and a compressor house therefor, is obviated. In addition the ancillary items of equipment normally needed when a gas recycle compressor is installed, such as a drive motor, power transformer, and instrumentation, are not required. There is also a saving in pipework for the plant as no provision for recycle of gas is needed. Although it is difficult to generalise, preliminary calculations suggest that the overall capital savings that can be achieved by adopting the process of the invention for an aldehyde hydrogenation plant with a throughput of 50,000 tonnes per year can be as much as about 10% compared with the cost of a conventionally designed aldehyde hydrogenation plant. Hence all of these factors have a significant effect on both capital and operating costs, both of which are significantly lower for a plant constructed to operate the process of the invention than for conventional multi-stage co-current or counter-current hydrogenation plants.

In order that the invention may be clearly understood and readily carried into effect two preferred processes in accordance therewith will now be described, by way of example only, with reference to FIGS. 1 and 2 of the accompanying drawings, each of which is a simplified flow diagram of an aldehyde hydrogenation plant constructed in accordance with the invention.

Figure 2:
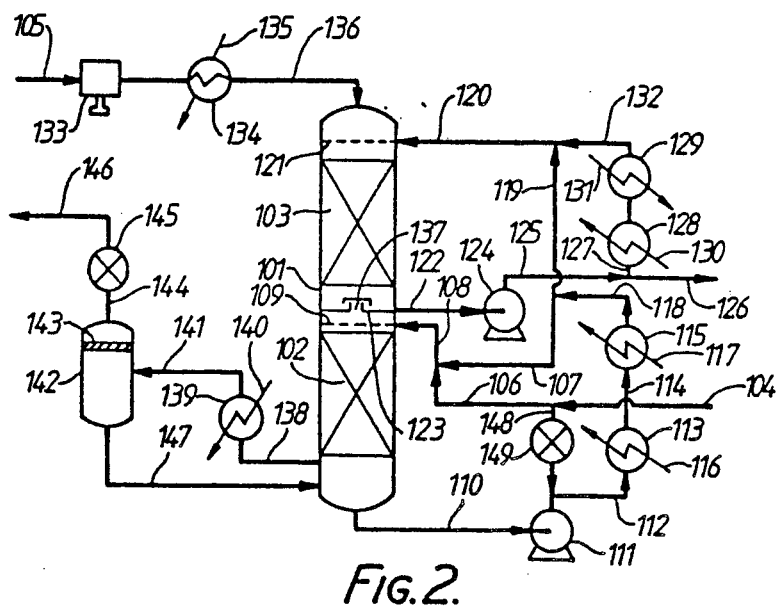
FIG. 2 is a simplified flow diagram similar to FIG. 1, but of a variation of the aldehyde hydrogenation plant.

It will be understood by those skilled in the art that FIGS. 1 and 2 are diagrammatic and that further items of equipment such as temperature and pressure sensors, pressure relief valves, control valves, level controllers and the like would additionally be required in a commerical plant. The provision of such ancillary items of equipment forms no part of the present invention and would be in accordance with conventional chemical engineering practice. Moreover it is not intended that the scope of the invention should be limited in any way by the precise methods of cooling and heating the various process streams, or by the arrangement of coolers, heaters, and heat exchangers, illustrated in FIGS. 1 and 2. Any other suitable arrangement of equipment fulfilling the requirements of the invention may be used in place of the illustrated equipment in accordance with normal chemical engineering techniques.

Referring to FIG. 1 of the drawings, a first reactor 1 is provided with an upper grid 2 which supports an upper bed 3 of a granular aldehyde hydrogenation catalyst. This catalyst is a prereduced nickel on alumina catalyst in the form of 1/16 inch (1.6 mm) spheres containing 61% of nickel (calculated as metal) in the 50% reduced form and having a surface area of 140 m$^2$/g as measured by the so-called BET method.

First reactor 1 is also fitted with a lower grid 4 which supports a lower bed 5 of the same nickel catalyst. Thermocouples (not shown) are buried in catalyst beds 3 and 5 and reactor 1 is thermally insulated. Steam heating coils (not shown) are provided under the thermal insulation in order to assist in heating reactor 1 at start up.

The space 6 below lower grid 4 is used to collect liquid emerging from the bottom of second bed 5. Such liquid is withdrawn by way of line 7 and is recycled by means of pump 8 and line 9 through heat exchanger 10. It is then fed through line 11 to a second heat exchanger 12 from which it is fed by way of lines 13, 14 to a static liquid distributor 15 positioned above upper bed 3 at the top of first reactor 1.

Reference numeral 16 indicates a feed line for heat exchanger 10 for supply of a heating medium (e.g. steam) or cooling water as need arises. Heat exchanger 12 is provided with a steam heating line 17. Aldehyde to be hydrogenated is supplied in line 18 and admixed with the liquid exiting heat exchanger 12. This is mainly product alcohol, but still contains a minor amount of hydrogenatable material. It acts as a diluent for the aldehyde. The rate of recycle in line 14 is selected so as to produce, upon admixture with the incoming aldehyde in line 18, a solution of aldehyde in the product alcohol which typically lies in the range of from about 5 mole % up to about 30 mole % and is selected such that the maximum temperature achieved in passage through first reactor 1 does not exceed the maximum permissible temperature for the hydrogenation reaction.

Part of the recycle stream in line 13 is withdrawn by way of line 19 and is passed by way of line 20 to a static liquid distributor 21 fitted near the top of a second reactor 22.

Hydrogen-containing gas is supplied to first reactor 1 in line 23. The source of such hydrogen-containing gas will be described further below.

A gas purge stream is taken from the space 6 below catalyst bed 5 in line 24. This is passed through a condenser 25 supplied with cooling water in line 26. Condensate is collected in gas-liquid separator 27 and is returned to line 7 in line 28. Reference numeral 29 indicates a mist eliminator pad. The resulting purge gas stream is taken in line 30 and is passed through a vent valve 31 which is used to control the pressure within the apparatus and the rate of discharge of purge gas in line 32.

Second reactor 22 is provided with an upper grid 33 which supports an upper bed 34 of hydrogenation catalyst and with a lower grid 35 which supports a lower bed 36 of the same catalyst. The catalyst of beds 34 and 36 may be the same as that of beds 3 and 5.

Make up hydrogen-containing feed gas is supplied to the plant in line 37, is compressed (if necessary) by means of gas compressor 38 and is then passed by way of heat exchanger 39 and line 40 to the upper end of second reactor 22. Reference numeral 41 indicates a steam heating line. The gas from line 40 and the feed in line 20 flow in co-current downwardly through second reactor 22. Substantially all of any hydrogenatable material remaining in the liquid in line 19 is hydrogenated in passage through second reactor 22. Hence what collects in the space 43 at the bottom of second reactor 22 below catalyst bed 36 is a mixture of hydrogen-containing gas and product alcohol. This is led in line 44 to a product recovery drum 45; hydrogen-containing gas therefrom is led by way of line 23 to the upper end of first reactor 1, as explained hereinabove. Liquid product alcohol which collects in drum 45 is recovered in line 46 and passed on for product purification in conventional manner, e.g. distillation in one or more fractional distillation stages.

Second reactor 22 can be operated, as described above, on a once-through basis as a single pass reactor. Alternatively the incoming intermediate reaction product in line 19 can be admixed with recycled product from product recovery drum 45. To this end a bypass line 47 is provided to enable recycle to be effected by means of recycle pump 48. This pumps crude liquid alcohol product by way of line 49 through heat exchanger 50 and then via line 51 to a further heat exchanger 52 for recycle in line 53 and admixture with intermediate reaction product in line 19. Reference numerals 54 and 55 indicate respective heating lines for heat exchangers 50 and 52 respectively, by means of which temperature control of the incoming liquid supplied in line 20 can be controlled.

Pump 48 and heat exchangers 50 and 52 can be used at start up of the plant to warm up the catalyst beds 34 and 36 by circulating alcohol through reactor 22 prior to introduction of aldehyde to the plant. Heat exchangers 10 and 12 and pump 8 can be used in a similar way to circulate alcohol through reactor 1 and warm its catalyst beds 3 and 5 to the desired starting temperature.

Product alcohol can be supplied to reactor 1 from product recovery drum 45, using pump 48, by way of line 56 under the control of valve 57.

If desired, a secondary aldehyde feed can be supplied by way of line 58, e.g. at start up of the plant.

The apparatus of FIG. 1 permits operation of the reactor 1 at a different lower pressure than reactor 22; in this case a pressure let down valve (not shown) can be provided in line 23 and a pump (not shown) can be provided in line 19. Alternatively reactor 22 can be operated at a lower pressure than reactor 1; in this case a pump (not shown) is provided in line 23 and a valve (also not shown) in line 19.

Instead of two reactor vessels 1 and 22 the plant of FIG. 2 has a single reactor 101 containing two hydrogenation catalyst beds 102 and 103. Catalyst bed 102 constitutes a first hydrogenation zone and catalyst bed 103 a second hydrogenation zone. Aldehyde to be hydrogenated is supplied in line 104 and hydrogen-containing feed gas in line 105.

The aldehyde feed flows from line 104 in line 106 and is admixed with a recycled alcohol stream in line 107. The admixed stream, containing typically from about 5 mole % to about 30 mole % aldehyde in a predominantly alcohol diluent, is fed in line 108 to a static liquid distributor 109 above catalyst bed 102. Intermediate reaction product is collected at the bottom of reactor 101 and is pumped by way of line 110, pump 111 and line 112 to a heat exchanger 113. Then the liquid intermediate reaction product, which contains typically from about 0.1 mole % to about 5 mole % chemically unsaturated hydrogenatable organic material, is fed in line 114 to a further heat exchanger 115. Reference numerals 116 and 117 indicate respective heating lines for heat exchangers 113 and 115. The liquid intermediate reaction product in line 118 is fed in part in line 107 as the recycle stream to catalyst bed 102 and in part via lines 119 and 120 to a further static liquid distributor 121 fitted above catalyst bed 103.

The chemically unsaturated hydrogenatable organic material remaining in the intermediate reaction product is substantially all hydrogenated to produce alcohol in passage through catalyst bed 103. Substantially pure product alcohol is recovered in line 122 from tray 123 and is pumped by means of pump 124 and lines 125 and 126 to a conventional alcohol purification section (not shown). If desired, part of the product alcohol can be passed by way of line 127 through heat exchangers 128 and 129, whose heating lines are indicated at 130 and 131 respectively, to line 132 for recycle to liquid distributor 121.

The hydrogen-containing feed gas in line 105 is compressed by means of gas compressor 133, heated in heat exchanger 134, whose steam heating line is indicated at 135, and supplied in line 136 to the top of reactor 101 above catalyst bed 103. Gas emerging from the bottom of catalyst bed 102 passes through an orifice 137 in tray 123 and into catalyst bed 102. A purge gas stream is taken from the bottom of reactor 101 below catalyst bed 102 in line 138 and is passed through a condenser 139 which is supplied with cooling water in line 140. The cooled gas is passed in line 141 to a gas-liquid separator 142 which is fitted with a spray eliminator pad 143. The purge gas passes out in line 144 through control valve 145 to a vent line 146. The condensate is returned from gas-liquid separator 142 to reactor 101 in line 147. reference numerals 148 and 149 represent a bypass line and bypass valve respectively for use at start up of the plant.

We claim:

1. A continuous process for hydrogenating an organic compound which can be hydrogenated in a liquid phase to a corresponding hydrogenation product, the process comprising:
   (a) providing a hydrogenation plant comprising first and second hydrogenation zones connected in series each containing a charge of a solid heterogeneous hydrogenation catalyst;
   (b) continuously supplying to an upper part of the first hydrogenation zone (i) a hydrogen-containing gas and (ii) a liquid phase containing the organic compound dissolved in a compatible diluent therefor;
   (c) maintaining the first hydrogenation zone under temperature and pressure conditions conductive to hdyrogenation;
   (d) allowing liquid phase to pass downwardly through the first hydrogenation zone;
   (e) continuously recovering an intermediate reaction product from a lower part of said first hydrogenation zone;
   (f) recovering a gaseous effluent from a lower part of the first hydrogenation zone;
   (g) supplying intermediate reaction product from step (e) in liquid form to an upper part of said second hydrogenation zone;
   (h) maintaining the second hydrogenation zone under temperature and pressure conditions conductive to hydrogenation;
   (i) allowing intermediate liquid reaction product to pass downwardly through said second hydrogenation zone;
   (j) supplying a hydrogen-containing feed gas to an upper part of the second hydrogenation zone;
   (k) recovering a gaseous effluent stream from a lower part of the second hydrogenation zone;
   (l) supplying material of the gaseous effluent stream of step (k) to form the hydrogen-containing gas of step (b);
   (m) recovering a liquid hydrogenation product containing stream from a lower part of the second hydrogenation zone; and
   (n) purging material of the gaseous effluent stream of step (f) from the hydrogenation plant.

2. A process according to claim 1, in which the hydrogen-containing feed gas of step (j) comprises a major molar amount of hydrogen and a minor molar amount of one or more inert gases.

3. A process according to claim 1 or claim 2, in which the compatible diluent comprises said hydrogenation product.

4. A process according to claim 3, which includes the further step of recycling a part of the liquid hydrogenation product stream of step (m) for admixture with the unsaturated organic compound to form the liquid phase (ii) of step (b).

5. A process according to any one of claim 4, in which the unsaturated organic compound is an aldehyde, and in which the hydrogenation product is an alcohol.

6. A process according to claim 5, in which the aldehyde is n-butyraldehyde, and in which the alcohol is n-butanol.

7. A process according to claim 5, in which the aldehyde contains from about 7 to about 17 carbon atoms.

8. A process according to claim 7, in which the aldehyde is 2-ethylhex-2-enal, and in which the alcohol is 2-ethylhexanol.

9. A process according to claim 7, in which the aldehyde is 2-propylhept-2-enal, and in which the alcohol is 2-propylheptanol.

10. A process according to claim 7, in which the aldehyde is undecanal, and in which the alcohol is undecanol.

11. A process according to claim 10, in which the entry temperature to the first hydrogenation zone lies in the range of from about 90° C. to about 220° C. and in which the pressure lies in the range of from about 5 to about 50 bar.

12. A continuous process for hydrogenating an organic compound selected from the group consisting of aldehydes, unsaturated hydrocarbons, unsaturated fatty acids, ketones and esters of unsaturated fatty acids to a corresponding hydrogenation product, the process comprising:
   passing the organic compound in a liquid phase successively through first and second hydrogenation zones containing a respective charge of a solid heterogeneous hydrogenation catalyst;
   passing a stream of hydrogen-containing gas through the second hydrogenation zone co-current with the flow of liquid phase organic compound;

maintaining the second hydrogenation zone under temperature and pressure conditions producing hydrogenation of the organic compound;

passing hydrogen-containing gas recovered from the second hydrogenation zone through the first hydrogenation zone co-current with the flow of liquid phase organic compound;

maintaining the first hydrogenation zone under temperature and pressure conditions producing hydrogenation of the organic compound;

purging gas from the first hydrogenation zone; and recovering the liquid hydrogenation product from the second hydrogenation zone.

* * * * *